United States Patent [19]

Haber et al.

[11] Patent Number: 4,767,413
[45] Date of Patent: Aug. 30, 1988

[54] DENTAL SYRINGE HAVING AN AUTOMATICALLY RETRACTABLE NEEDLE

[75] Inventors: Terry M. Haber, Lake Forest; William H. Smedley, Lake Elsinore; Clark B. Foster, El Toro, all of Calif.

[73] Assignee: Habley Medical Technology Corporation, Laguna Hills, Calif.

[21] Appl. No.: 39,715

[22] Filed: Apr. 20, 1987

[51] Int. Cl.$^4$ .............................................. A61M 5/32
[52] U.S. Cl. ..................................... 604/198; 604/232
[58] Field of Search ............... 604/198, 197, 232, 233, 604/234, 235, 139

[56] References Cited

U.S. PATENT DOCUMENTS

| | | | |
|---|---|---|---|
| 3,055,362 | 9/1962 | Uytenbogaart | 604/197 X |
| 3,066,670 | 12/1962 | Stauffer | 604/139 |
| 3,136,313 | 6/1964 | Enstrom et al. | 604/139 |
| 3,306,290 | 2/1962 | Weltman | 604/197 |
| 3,605,744 | 9/1971 | Dwyer | 604/139 |

Primary Examiner—John D. Yasko
Attorney, Agent, or Firm—Morland C. Fischer

[57] ABSTRACT

A disposable dental syringe of the type having a prefilled ampule of fluid medication and a double ended hypodermic needle arranged in spaced, axial alignment with the ampule. The ampule may be moved axially through the cylinder of the syringe until the proximal end of the needle penetrates the ampule and the distal end of the needle extends outwardly from the cylinder for administering an injection. The ampule is locked in the distal position so that an injection may be administered. Upon completing the injection, the ampule is released from the distal position and moved proximally through the cylinder, so that the distal end of the needle is automatically retracted within the cylinder. The syringe may now be safely discarded with the hypodermic needle completely shielded within the cylinder, so as to eliminate the necessity of handling and/or breaking the needle and, thereby, avoiding the possibility of an accidental needle strike.

26 Claims, 6 Drawing Sheets

DENTAL SYRINGE HAVING AN AUTOMATICALLY RETRACTABLE NEEDLE

BACKGROUND OF THE INVENTION

1. Field of the Invention

This invention relates to a dental syringe of the type having a pre-filled ampule of fluid medication and a double ended hypodermic needle which may be automatically relocated from a distally extended position, at which to inject the fluid medication at a targeted tissue area, to a proximally retracted position, at which the needle is withdrawn within and shielded by the cylinder of the syringe.

2. Prior Art

Dental syringes of the type having a pre-filled ampule of fluid medication and a double ended hypodermic needle are well-known in the art for injecting such medication from the ampule to a targeted tissue area of the patient. For example, reference may be made to U.S. Pat. No. 3,306,290 issued Feb. 28, 1967 to H. S. Weltman. However, at the completion of the injection, the needle is typically locked in an axially extended position projecting outwardly from a distal bore formed through the syringe cylinder.

In some cases, the syringe may be used to treat a patient having a communicable disease. Prior to disposing of the syringe, the hypodermic needle is frequently broken or destroyed to prevent reuse. Dental office workers are especially susceptible to accidental and potentially infectious needle strikes due to the careless handling or breaking of the needle and disposing of the syringe after use. The resulting mini-accident caused by an accidental needle strike typically requires a blood test for such diseases as AIDS and hepatitis. The corresponding cost and inefficiency of testing dental office workers who have received such an inadvertent needle strike result in considerable waste, which may be particularly damaging to a dental facility which is striving for economy.

SUMMARY OF THE INVENTION

Briefly, a disposable dental syringe is disclosed of the type having a pre-filled ampule of fluid medication (e.g. novocain) and a double ended, hypodermic needle which communicates with the ampule to deliver the contents thereof to a targeted tissue area. The syringe includes a piston stem which is connected to a plunger at a proximal end of the ampule. The piston stem and ampule are connected together at the interior of a hollow retaining collar having a conical locking skirt extending around the periphery thereof. The barrel or cylinder of the syringe includes a pair of spring-like locking arms which are hingedly connected to the cylinder and normally biased outwardly therefrom. The proximal end of the cylinder includes a peripheral flange having a pair of angled ears. When the dentist locates his fingers below the angled ears, equal and opposite compressive forces are generated by which to cause the locking arms to pivot inwardly through respective longitudinally extending slots formed in the cylinder.

A needle cartridge is located within the cylinder ahead of the ampule. The cartridge comprises a hollow sleeve having a plug at a distal end thereof and a needle supporting and aligning member at the proximal end. A compression spring is retained within the sleeve by and between the distal end plug and the supporting and aligning member. A hypodermic needle is coaxially aligned with the compression spring and the sleeve. The proximal end of the needle is connected to and extended through the supporting and aligning member, and the distal end of the needle is supported by the distal end plug. The needle supporting and aligning member includes a receptacle for receiving and locking the sealed end cap of the ampule when the ampule is axially and distally advanced into engagement with the needle cartridge.

In operation, the dentist's fingers are located below the ears of the proximal flange of the cylinder (to pivot the locking arms inwardly into the cylinder). The retaining collar and the ampule therewithin are advanced axially and distally through the syringe cylinder and into the sleeve of the needle cartridge, whereby to lock the end cap of the ampule within the receptacle of the needle supporting and aligning member and locate the locking skirt of the retaining collar below the spring-like locking arms of the syringe cylinder. With the retaining collar and ampule retained by the locking arms at the distally advanced position within the sleeve of the needle cartridge, the proximal end of the needle penetrates the sealed end cap of the ampule and the spring is compressed within the sleeve to extend the distal end of the needle outwardly from the syringe cylinder for administering an injection. The piston stem is forced axially through the ampule, whereby fluid medication is delivered, by way of the needle, to a target area of the patient.

The dentist then removes his fingers from the syringe. Accordingly, the spring biased locking arms of the syringe cylinder pivot away from the cylinder and out of engagement with the conical locking skirt of the retaining collar. The compression spring is free to return to the relaxed condition whereby to drive the ampule and retaining collar axially and proximally through the sleeve of the needle cartridge. The proximal movement of the ampule through the sleeve causes the distal end of the hypodermic needle to be automatically withdrawn into the cylinder. Hence, the hypodermic needle is relocated from a distally extended position, at which to inject the medication from the ampule to the patient, to a proximally retracted position, at which the needle is withdrawn within and shielded by the syringe cylinder. The syringe may now be safely discarded with the needle retracted within and shielded by the cylinder so as to eliminate the need for the dentist to handle or destroy the needle and reduce the likelihood of exposing a dental worker to an accidental needle strike.

DESCRIPTION OF THE PREFERRED EMBODIMENT

Figure 1:
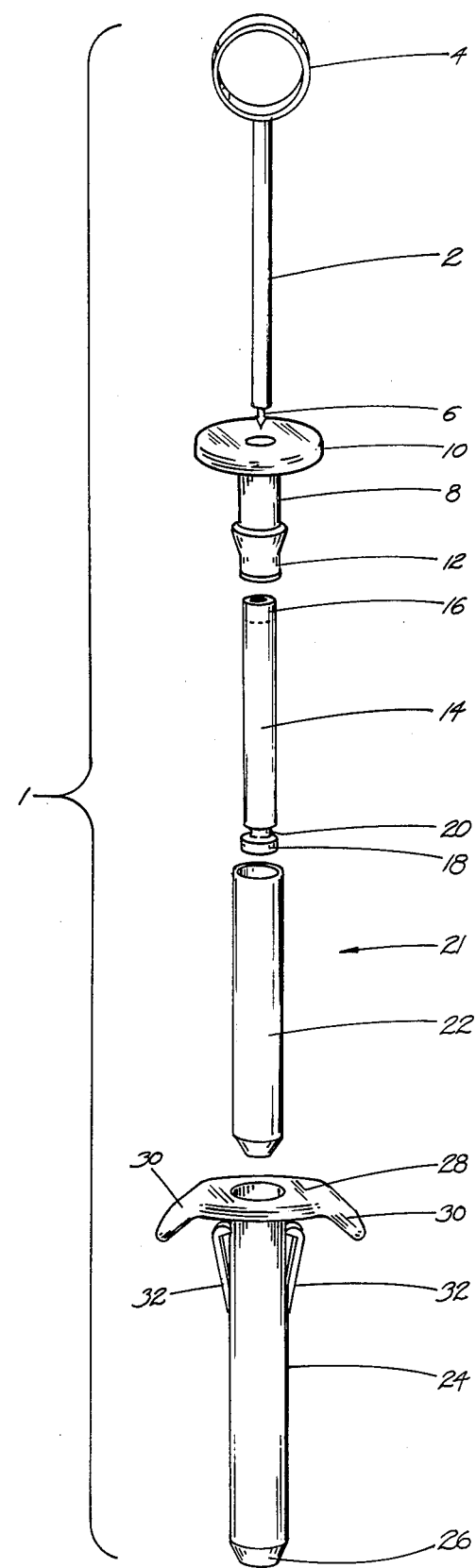
FIG. 1 is an exploded view of a dental syringe which forms one embodiment of the present invention.

A dental syringe which forms a first embodiment of the present invention is best described while referring to the drawings where, in FIG. 1, there is shown an exploded view of the syringe 1. The syringe 1 comprises a piston stem 2 having a finger loop 4 affixed to a proximal end thereof and a sharp metal tip 6 protruding outwardly from a distal end. A hollow retaining collar 8 has a flange 10 coextensively formed around the proximal end thereof and a conical locking skirt 12 located at the distal end. A pre-filled ampule 14 is provided having a rubber plunger 16 located at a proximal end thereof and a sealed, metal end cap 18 extending from the distal end. End cap 18 is spaced from the body of ampule 14 by a relatively narrow neck 20. Ampule 14 is of conventional design and is typically fabricated from glass, or the like. As will be known to those skilled in the art, ampule 14 contains a fluid medication, such as novocain.

A needle cartridge 21 (best shown in FIG. 2) includes a cylindrical sleeve 22 that is sized to receive the ampule 14 through an open proximal end thereof. As will soon be explained, ampule 14 is adapted for axial and reciprocal movement through the sleeve 22 of cartridge 21.

A hollow syringe barrel or cylinder 24 is sized to accommodate the needle cartridge 21 therewithin. Cylinder 24 includes an open proximal end, through which the retaining collar 8 is moved and the needle cartridge 21 is located, and a substantially closed distal end wall 26 past which a hypodermic needle (not shown) is to be extended or retracted. A flange 28 is formed around the open proximal end of cylinder 24. Flange 28 includes a pair of oppositely disposed ears 30 which are angled distally from the body of flange 28 to perform an important finger locating function which will be described in greater detail when referring to FIGS. 3–5. A pair of spring-like locking arms 32 are hingedly attached to opposite sides of cylinder 24 and adapted to selectively pivot into and out of engagement with the conical locking skirt 12 of retaining collar 8 to perform an important position securing function which will also be described in greater detail when referring to FIGS. 3–5.

Figure 2:
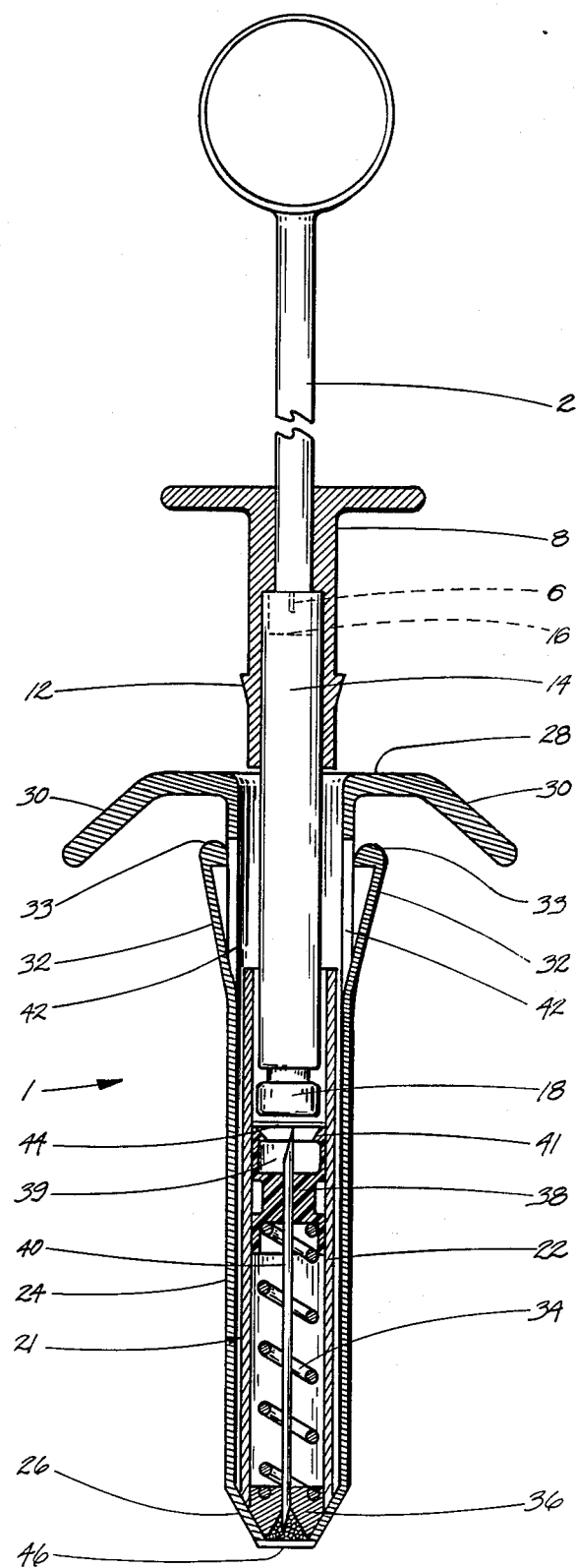
FIG. 2 is a partial cross-section showing the syringe of FIG. 1 in the assembled relationship.

In the assembled relationship of FIG. 2, the syringe 1 is shown with the hollow retaining collar 8 receiving the piston stem 2 through the proximal end thereof and the ampule 14 through the distal end, such that the metal tip 6 of piston stem 2 is moved into contact with the plunger 16 of ampule 14 so as to enable stem 2 to be connected to ampule 14 at the interior of retaining collar 8. Also shown is the needle cartridge 21 located at the distal end of the syringe cylinder 24. The needle cartridge 21 is axially aligned for engagement with the sealed end cap 18 of ampule 14 when the ampule is moved into and distally through the sleeve 22 of cartridge 21.

Located at the distal end of the sleeve 22 of needle cartridge 21 is a compression spring 34. Compression spring 34 extends between and is retained by a distal end plug 36 and a needle supporting and aligning member 38. Distal end plug 36 lies within the bore of the distal end wall 26 of cylinder 24. Needle supporting member 38 is spaced from the proximal end of sleeve 22. Needle supporting member 38 includes a hollow receptacle 39 which terminates at an annular lip 41. As will soon be explained, the receptacle 39 of supporting member 38 is adapted to receive therewithin the end cap 18 of ampule 14, so that the lip 41 of receptacle 39 may lock the end cap 18 within the receptacle 39. Needle cartridge 21 also includes a double ended hypodermic needle 40 which is supported at opposite ends thereof by the distal end plug 36 and the needle supporting and aligning member 38. More particularly, needle 40 is coaxially arranged with respect to the spring 34 and the sleeve 22 of cartridge 21. A proximal end of the needle 40 extends through and is retained by the needle supporting member 38 so as to be aligned for contact with and penetration of the sealed end cap 18 of ampule 14 (when such end cap is received and locked within the receptacle 39 of needle supporting member 38), and the distal end of needle 40 extends through a hole formed in the distal end plug 36 of cartridge 21 for expulsing the fluid contents of ampule 14.

Extending across the top of the receptacle 39 of needle supporting member 38 is a seal 44. Extending across the distal end wall 26 of syringe cylinder 24 is a seal 46. The seals 44 and 46 preserve the sterility of needle 40 within the environment of needle cartridge 21 by isolating the opposite ends of the needle from potentially contaminating external airflow. Seals 44 and 46 are formed from rubber, or the like, and are penetrated by the respective ends of needle 40 when the end cap 18 of ampule 14 is received by the receptacle 39 and needle 40 is axially advanced past the distal end wall 26 of cylinder 24.

The spring-like locking arms 32 of cylinder 24 are normally biased to extend outwardly and away from the syringe cylinder 24. Each locking arm 24 terminates at an inwardly projecting locking finger 33. To permit the locking arms 32 to be pivoted against their normal bias in a direction toward the cylinder 24, a pair of oppositely disposed, longitudinally extending slots 42 are formed in the side of cylinder 24 through which the locking fingers 33 of arms 32 may be rotated.

Figure 3:
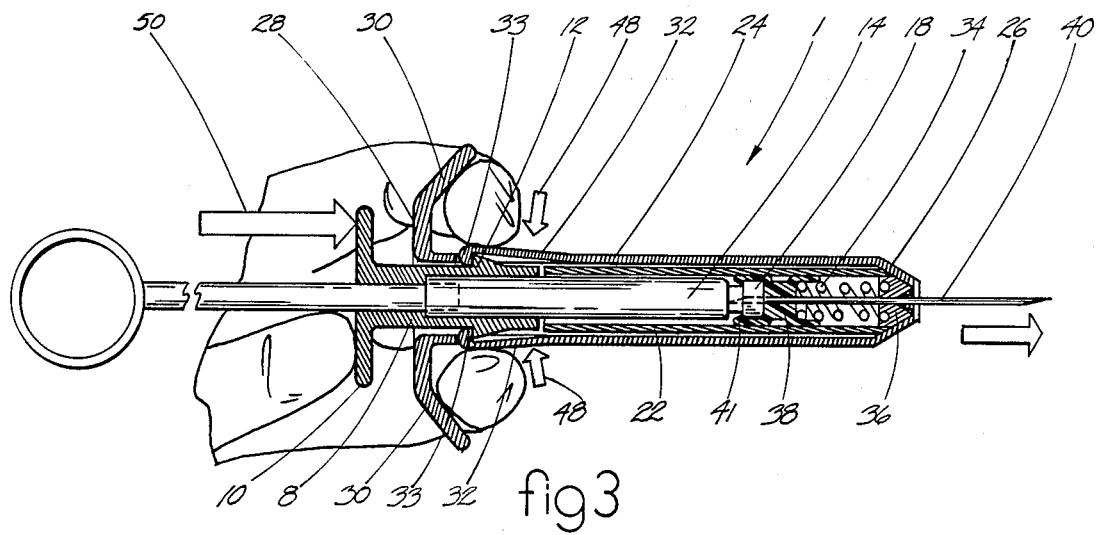
FIGS. 3-5 illustrate the steps for operating the dental syringe of FIG. 1 for relocating a hypodermic needle from a distally extended position to a proximally retracted position.
Figure 4:
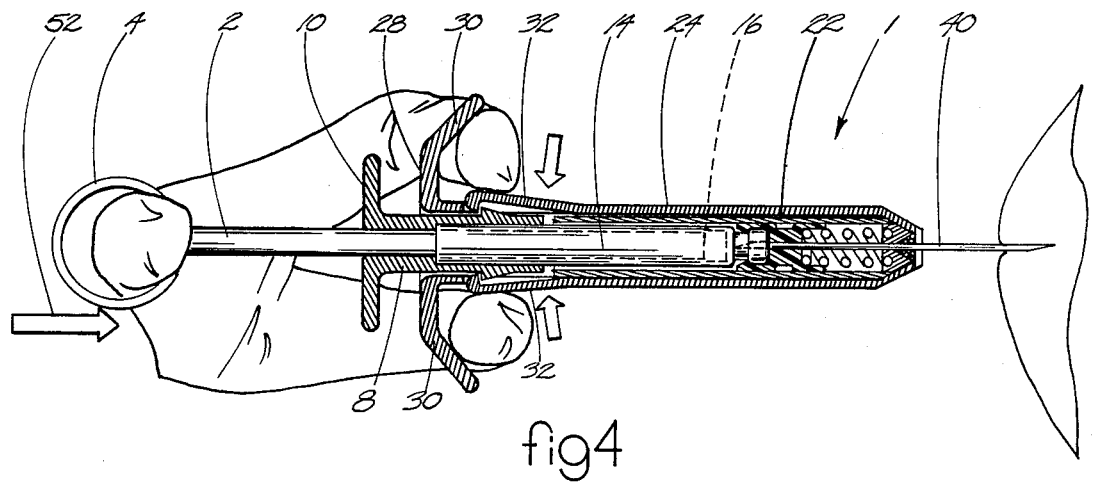
Figure 5:
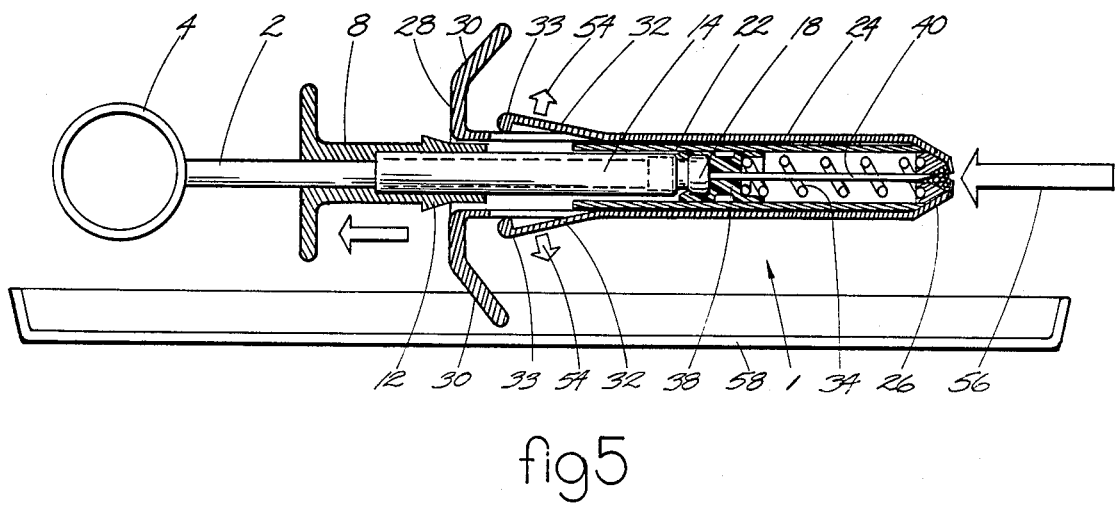

The operation of the dental syringe 1 of the present invention is now described while referring to FIGS. 3–5 of the drawings. As seen in FIG. 3, the dentist locates a pair of his fingers (e.g. the index and middle finger) under the ears 30 of flange 28 at the proximal end of syringe cylinder 24. By virtue of the angled ears 30 of flange 28, the dentist's fingers are automatically positioned so as to apply equal and opposite compressive forces (in the directions indicated by the reference arrows 48) against the locking arms 32 of cylinder 24. Accordingly, the locking arms 32 are caused to pivot against their normal spring bias, such that the respective locking fingers 33 are rotated through the slots (designated 42 in FIG. 2) formed in the cylinder 24.

The dentist, using his thumb, then depresses the flange 10 at the proximal end of retaining collar 8 to advance the collar 8 axially and distally (in the direction of reference arrow 50) through the open proximal end of cylinder 24. The retaining collar 8 is locked in the axially advanced position within cylinder 24 when the locking skirt 12 thereof is snapped into receipt below the inwardly extending locking fingers 33 of locking arms 32. The distal movement of retaining collar 8 causes a corresponding advancement of ampule 14 axially and distally through the sleeve 22 of needle cartridge 21 until the end cap 18 of ampule 14 is received within the receptacle (designated 39 in FIG. 2) of needle supporting and aligning member 38. The ampule 14 is locked in the axially advanced position of sleeve 22 when the end cap 18 thereof is snapped into receipt below the annular lip 41 of the receptacle 39 of needle supporting member 38. The axial and distal advancement of ampule 14 through the sleeve 22 of cartridge 21 also moves the ampule (and the fluid contents thereof) into communication with the hypodermic needle 40, such that the proximal end of the needle penetrates the sealed end cap 18 of ampule 14 when the ampule is received within the receptacle 39. Moreover, the distal end of needle 40 is moved outwardly from the syringe cylinder 24 and past the distal end wall 26 thereof. Likewise, the needle supporting and aligning member 38 is driven axially and distally through sleeve 22, whereby compression spring 34 is compressed (against its normal bias) between needle supporting member 38 and distal end plug 36 of cartridge 21.

In FIG. 4, the dentist leaves his fingers below the angled ears 30 of flange 28, but now relocates his thumb from the flange 10 of retaining collar 8 to the finger loop 4 at the proximal end of piston stem 2. With the locking skirt 12 of retaining collar 8 remaining locked in the axially advanced position within cylinder 24 by means of locking arms 32, the dentist forces the piston stem 2 distally (in the direction of reference arrow 52) through the retaining collar 8, so that an axial force is transferred from finger loop 4 to the plunger 16 at the proximal end of ampule 14. Accordingly, the plunger 16 is moved axially and distally through ampule 14 so that the fluid contents of the ampule can be injected into the targeted tissue area of the patient by means of needle 40.

In FIG. 5, after the contents of ampule 14 have been expulsed to the patient and the needle 40 has been removed from the targeted tissue area, the dentist removes his fingers from below the angled ears 30 of flange 28 and his thumb from the finger loop 4. The needle 40 is immediately and automatically retracted completely within the syringe cylinder. More particularly, without the dentist's fingers engaging the locking arms 32 below the ears 30 of flange 28, the locking fingers 33 of arms 32 are disengaged from the conical locking skirt 12 of retaining collar 8.

That is to say, the normal spring bias of locking arms 32 causes such arms to pivot (in the direction of the reference arrows 54) outwardly and away from the syringe cylinder 24. With the locking fingers 33 detached from the locking skirt 12 and the end cap 18 of ampule 14 remaining locked within the receptacle of the needle supporting and aligning member 38, the previously compressed spring 34 is now free to return to its relaxed state. However, the potential energy stored within the spring 34 is sufficient to drive the piston assembly, comprising the interconnection of needle 40, needle supporting member 38, ampule 14, piston stem 2 and finger loop 4, axially and proximally through the sleeve 22 of needle cartridge 21. Accordingly, the needle 40 is withdrawn through the distal end wall 26 of syringe cylinder 24 so as to be retracted (in the direction of reference arrow 56) completely within the needle cartridge sleeve 22. Thus, by the time that the syringe 1 is placed in a dental tray 58, the needle 40 will have been relocated from a distally extended position, at which to deliver an injection to a targeted area, to a proximally retracted position, at which the needle 40 is withdrawn within and shielded by the cylinder 24 of syringe 1.

The syringe 1 may now be discarded in a normal fashion. However, by virtue of the present invention, the syringe is rendered safe by first withdrawing and locking the hypodermic needle 40 within cylinder 24, such that the needle is completely shielded by the cylinder. Accordingly, the syringe 1 is in a condition to permit a safe disposal without having to handle or cut the needle and without exposing the dentist to an accidental needle strike and to the possible spread of a contagious disease.

Figure 7:
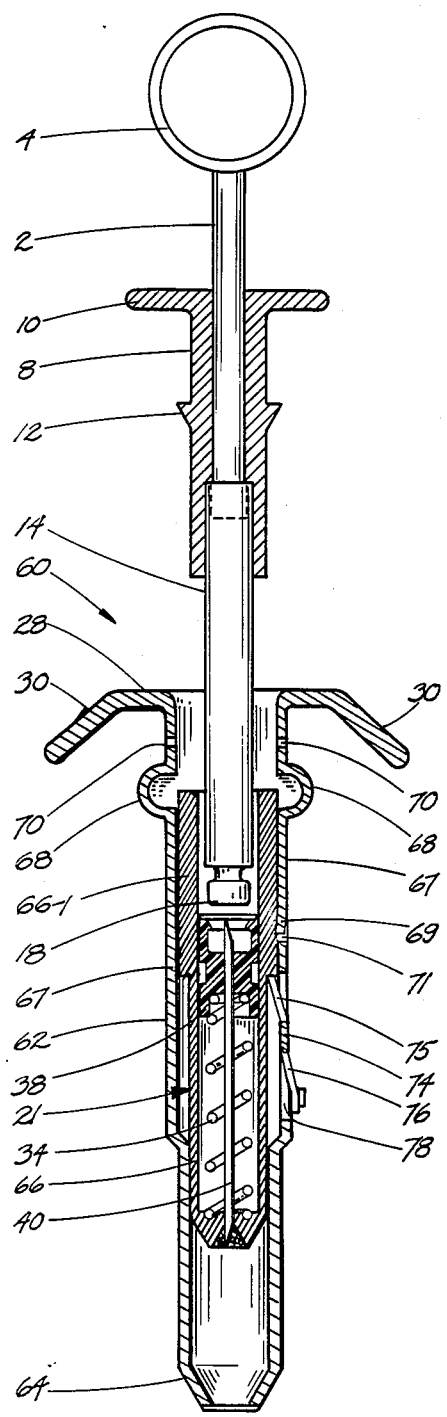
FIGS. 7-10 illustrate the steps for operating the syringe of FIG. 6.
Figure 6:
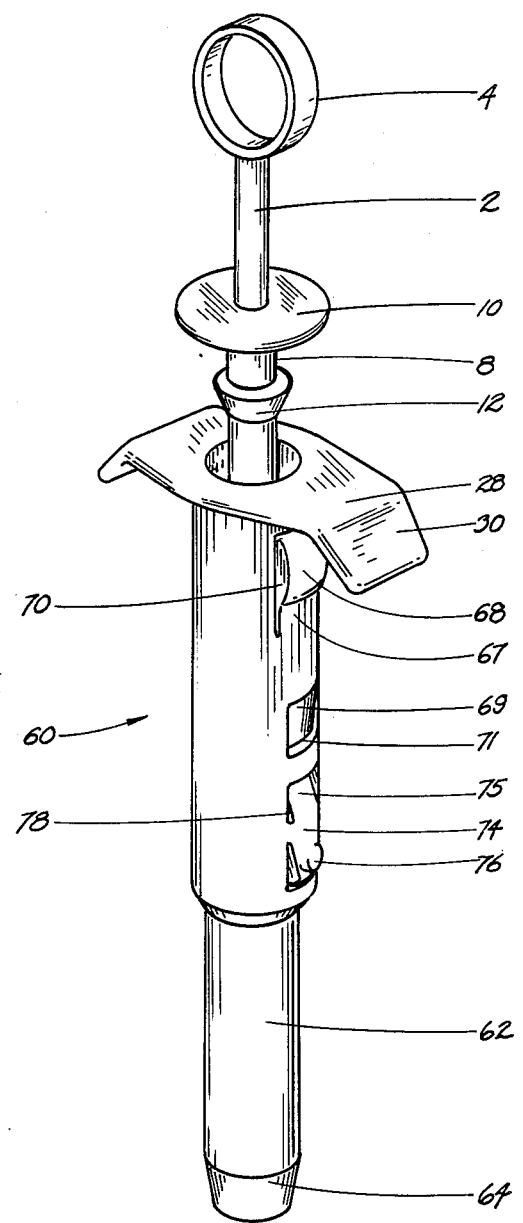
FIG. 6 is an isometric view of a dental syringe which forms an alternate embodiment of the present invention.

An alternate embodiment of a dental syringe according to the present invention is described in FIGS. 6-10 of the drawings. The syringe 60 includes some of the same elements as the syringe 1 illustrated in FIGS. 1-5. Therefore, and in these cases, identical reference numerals will be used, and a detailed description of such elements will be omitted. Referring concurrently to FIGS. 6 and 7, the syringe 60 is shown at rest, including a piston stem 2 having a finger loop 4 at a proximal end thereof and a sharp metal tip (not shown) at a distal end to be connected to the plunger of a pre-filled ampule (best shown in FIG. 7). The piston stem 2 and the ampule 14 are interconnected within a hollow retaining collar 8. Retaining collar 8 has a flange 10 extending around the proximal end thereof and a coextensively formed conical locking skirt 12 extending around the distal end. The barrel or cylinder 62 of syringe 60 has an open proximal end and a substantially closed, tapered distal end wall 64. A needle cartridge 21 (also best shown in FIG. 7) is loaded through the open proximal end of cylinder 62.

Needle cartridge 21 comprises a double ended hypodermic needle 40 which is coaxially aligned with a compression spring 34 and a hollow sleeve 66. The sleeve 66 includes a proximal end 66-1 of relatively wide diameter and distal end of relatively narrow diameter. The ampule 14 is loaded through the proximal end of the cylinder 62 after needle cartridge 21, such that the proximal end of the hypodermic needle 40 of cartridge 21 is axially aligned with and spaced from the sealed end cap 18 of ampule 14.

A flange 28 is formed about the open proximal end of cylinder 62. Flange 28 includes a pair of oppositely disposed ears 30 which, as in the syringe of FIGS. 1-5, are angled distally from the body of flange 28 to perform an important finger locating function. A pair of spring-like locking arms 67 are hingedly attached at distal ends thereof to opposite sides of cylinder 62. The proximal ends of locking arms 67 terminate at respective arcuate-shaped locking cups 68. The locking arms 67 are adapted to pivot laterally and against their normal bias, such that the locking cups 68 can be moved into engagement with the conical locking skirt 12 of retaining collar 8 to lock the collar and the ampule 14 at a distally advanced position within the interior of syringe cylinder 62 (to be described in greater detail when referring to FIG. 9). To facilitate the movement of locking cups 68 into engagement with locking skirt 12, a pair of oppositely disposed, longitudinally extending slots 70 are formed in the side of cylinder 62 through which the locking cups 68 may rotate.

Conextensively formed with and connected at a proximal end thereof to the syringe cylinder 62 is a resilient locking tab 69. Locking tab 69 is angled inwardly from the cylinder 62, so that, in its normal bias, the distal end of locking tab 69 projects through a slot 71 formed in the side of cylinder 62 for engaging the needle cartridge 21 (the details of which to be described when referring hereinafter to FIGS. 9 and 10).

Hingedly attached to one side of the syringe cylinder 62 is a needle cartridge stop 74. Stop 74 includes a pair of legs 75 and 76 which extend in opposite directions from the hinge attachment to cylinder 62. The needle cartridge stop 74 is adapted to pivot, such that one of the legs (e.g. 75) may be moved into engagement with the proximal end 66-1 of the needle cartridge sleeve 66 to block the distal movement of the needle cartridge 21 through the cylinder 62. To facilitate the movement of an arm 75 of cartridge stop 74 into engagement with cartridge sleeve 66, an opening 78 is formed through the side of cylinder 62 through which such arm may rotate.

The operation of the syringe 60 is now disclosed while referring to FIGS. 7-10 of the drawings. In the at rest configuration of FIG. 7, the ampule 14 and needle cartridge 21 are arranged in spaced axial alignment with one another, and the needle cartridge 21 is spaced proximally from the tapered end wall 64 of syringe cylinder 62. The relatively proximal location of the cartridge sleeve 66 within syringe cylinder 62 forces the resilient locking tail 69 to be retained, against its normal bias, outwardly from the slot 71. The locking arms 67 are in their normally biased position with the locking cups 68 thereof located out of engagement of the locking skirt 12 of retaining collar 8. The needle cartridge stop 74 is pivoted, such as that one leg 75 is rotated through opening 78 to engage the needle cartridge 21 at the interface of the relatively wide and narrow, proximal and distal ends of cartridge sleeve 66. As should be apparent, the distal movement of the needle cartridge 21 through syringe cylinder 62 is blocked when the leg 75 of needle cartridge stop 74 is rotated into engagement with the cartridge sleeve 66 below the relatively wide proximal end 66-1 thereof.

Figure 8:
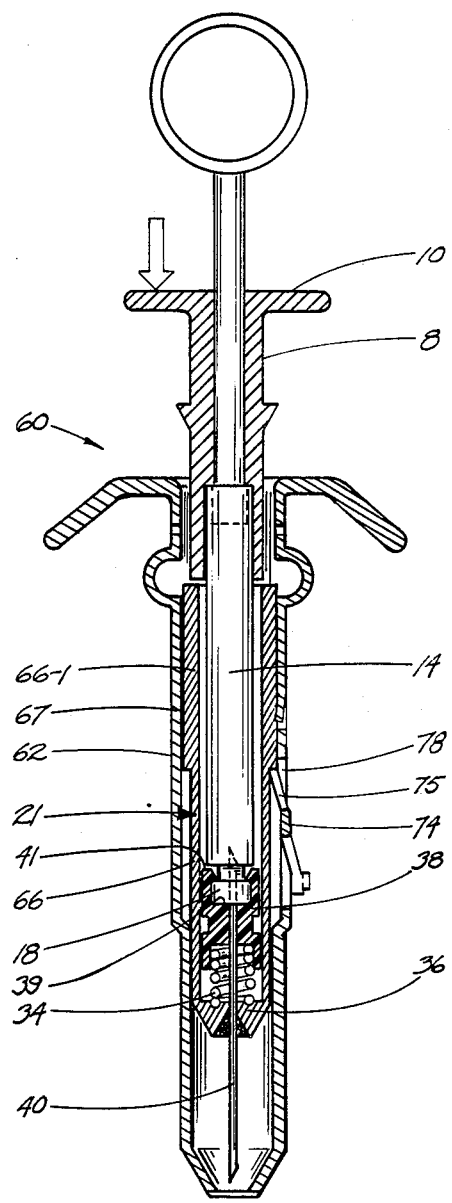

Referring now to FIG. 8 of the drawings, and with the needle cartridge 21 still locked in a relatively proximal position within the cylinder 62 of syringe 60 by the rotation of the arm 75 of needle cartridge stop 74 through opening 78, the dentist locates his thumb on the flange 10 of retaining collar 8. Flange 10 is then depressed to advance the collar 8 axially through the proximal end of cylinder 62. The axial advancement of collar 8 causes a corresponding axial and distal advancement of ampule 14 through the sleeve 66 of needle cartridge 21 until the end cap 18 of ampule 14 is snapped into receipt within the receptacle 39 and below the annular lip 41 thereof at the proximal end of the needle supporting and aligning member 38. Accordingly, the proximal end of the hypodermic needle 40 penetrates the seal of end cap 18, so that needle 40 and ampule 14 are placed in fluid communication with one another.

The axial advancement of ampule 14 through needle cartridge sleeve 66 to locate the end cap 18 within the receptacle 39 of needle supporting member 38 causes the spring 34 at the distal end of needle cartridge sleeve 66 to be momentarily compressed. Moreover, the distal end of the needle 40 is momentarily advanced outwardly from the needle cartridge 21 and past the distal end plug 36 thereof. However, by virtue of the interaction between needle cartridge stop 74 and the relatively wide proximal end 66-1 of needle cartridge sleeve 66, the needle cartridge 21 cannot be displaced distally through cylinder 62 in response to the axial force which is generated when the ampule 14 is moved distally through cartridge sleeve 66. Therefore, and as an advantageous benefit of needle cartridge stop 74, the maximum axial advancement of needle 40 from needle cartridge 21 is limited when cartridge 21 is engaged by stop 74. That is to say, the distal cutting end of needle 40 is completely contained within and shielded by the syringe cylinder during the connection of ampule 14 to needle 40, whereby to eliminate the possibility of subjecting the dentist to an accidental needle strike.

Figure 9:
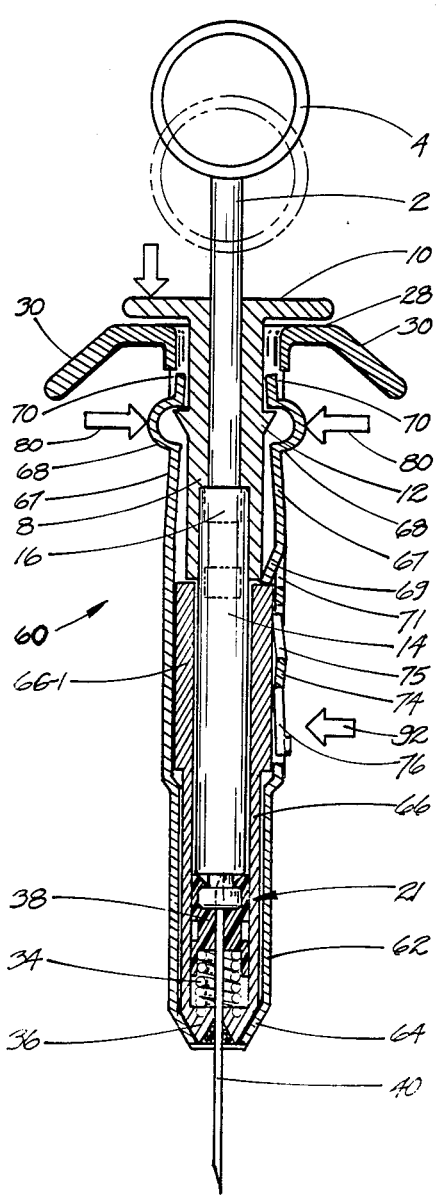

In FIG. 9 of the drawings, the syringe 60 is shown in the injection state. More particularly, the dentist locates his index and middle fingers under the ears 30 of flange 28 and his thumb on the flange 10 of retaining collar 8. By virtue of the angled ears 30 of flange 28, the dentist's index and middle fingers are automatically positioned so as to apply equal and opposite compressive forces (in the directions indicated by reference arrows 80) against the locking arms 67 of syringe cylinder 62. Accordingly, the locking arms 67 are caused to pivot against their normal spring bias, such that the respective locking cups 68 thereof are rotated through the slots 70 formed in the syringe cylinder 62.

With his opposite hand, the dentist depresses the leg 76 of needle cartridge stop 74 (in the direction represented by reference arrow 92). Accordingly, the stop 74 is pivoted, such that the leg 75 thereof, which was previously located at the interface of the relatively wide and narrow ends of the sleeve 66 of needle cartridge 21, is rotated out of engagement with cartridge 21, such that the cartridge may now be moved axially through the cylinder 62.

The dentist, using his thumb, then depresses the flange 10 at the proximal end of retaining collar 8 to axially and distally advance the retaining collar through the cylinder 62. The retaining collar 8 is locked in the axially advanced position within cylinder 62 when the locking skirt 12 thereof is snapped into receipt below the inwardly extending locking cups 68 of locking arms 67. The distal movement of retaining collar 8 causes a corresponding advancement of ampule 14 and needle cartridge 21 axially and distally through cylinder 62. The distal relocation of needle cartridge 21 through cylinder 62 is terminated when the distal end of cartridge 21 is seated upon the tapered distal end wall 64 of cylinder 62. The relocation of cartridge 21 to the distal end of cylinder 62 allows the resilient locking tab 69 to rotate through the opening 71 formed in cylinder 62 to return to its normally biased position. In its normally biased position, the locking tab 69 projects slightly inward into the cylinder 62 to engage the proximal end 66-1 of the sleeve 66 of needle cartridge 21 to thereby prevent the proximal movement of cartridge 21 past tab 69 and through cylinder 62, for an important advantage which will be discussed when referring to FIG. 10.

The distal movement of ampule 14 through cylinder 62 causes the needle supporting and aligning member 38 to be driven axially and distally through the sleeve 66 of needle cartridge 21, such that compression spring 34 is compressed between member 38 and the distal end plug 36 of cartridge 21. Accordingly, the distal cutting end of needle 40 is moved outwardly from the syringe cylinder 62 and past the distal end wall 64 thereof.

With his fingers remaining below the angled ears 30 of flange 28, the dentist relocates his thumb from the flange 10 of retaining collar 8 to the finger loop 4 at the proximal end of piston stem 2. With the locking skirt 12 of retaining collar 8 locked within the retaining cups 68 of locking arms 67 (to prevent the proximal displacement of retaining collar 8), the dentist forces the piston stem 2 distally through the retaining collar 8, such that an axial force is transferred from the finger loop 4 to the plunger 16 at the proximal end of ampule 14. The plunger 16 is thereby moved axially and distally through ampule 14, so that the fluid contents of the ampule can be injected into a targeted tissue area of the patient by means of the extended needle 40.

Figure 10:
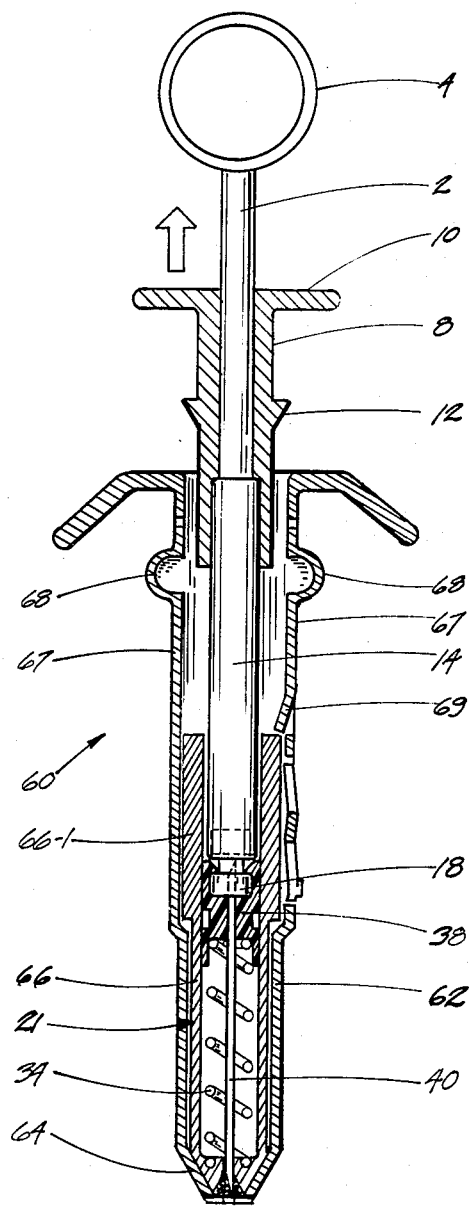

FIG. 10 of the drawings shows the syringe 60 with the hypodermic needle 40 retracted within the cylinder 62. More particularly, after the contents of ampule 14 have been expulsed to the patient, the dentist removes his fingers from below the angled ears 30 of flange 28 and his thumb from the finger loop 4. The needle 40 is immediately and automatically retracted completely within the cylinder 62. Without the dentist's fingers engaging the locking cups 68 of locking arms 67 below the ears 30 of flange 28, the locking cups 68 are disengaged from the conical locking skirt 12 of retaining collar 8. That is, the normal spring bias of locking fingers 67 causes such fingers to pivot outwardly and away from the locking skirt 12.

With the locking cups 68 detached from the locking skirt 12 and the end cap 18 of ampule 14 remaining locked within the receptacle of needle supporting and aligning member 38, the previously compressed spring 34 is now free to return to its relaxed state. However, the potential energy stored within spring 34 is sufficient to drive the piston assembly, comprising the interconnection of needle 40, needle supporting member 38, ampule 14, piston stem 2, and finger loop 4, axially and proximally through the sleeve 66 of needle cartridge 21. Accordingly, the needle 40 is withdrawn through the distal end wall 64 of syringe cylinder 62 so as to be retracted completely within the needle cartridge sleeve 66. Thus, by the time that the syringe 60 is placed within a dental tray, the needle 40 will have been relocated from an extended distal position relative to syringe cylinder 62 to a retracted proximal position within said cylinder so as to permit the safe disposal of the syringe.

As previously disclosed when referring to FIG. 9, the locking tab 69 projects into the syringe cylinder 62 so as to engage the proximal end 66-1 of the needle cartridge 21. By virtue of this arrangement, the dentist may remove the ampule 14 through the open proximal end of the cylinder 62. However, locking tab 69 blocks the proximal displacement of needle cartridge 21 through the syringe cylinder 62 when the ampule 14 is removed. Therefore, the ampule 14 may be pulled proximally through cylinder 62 relative to needle cartridge 21, so as to enable the dentist to easily detach the end cap 18 of ampule 14 from the receptacle of the needle supporting and aligning member 38. Accordingly, the dentist may replace the previously removed ampule with a new ampule by snapping the ampule into the receptacle of needle supporting and aligning member 38, such that hypodermic needle 40 is placed in fluid communication therewith.

It will be apparent that while a preferred embodiment of the present invention has been shown and described, various modifications and changes may be made without departing from the true spirit and scope of the invention. For example, although the syringe of this invention has been described with particular reference to a dental syringe, it is to be understood that this is not to be regarded as a limitation, and the claims which are appended hereto are applicable to other suitable types of syringes where it is desirable to relocate a hypodermic needle from a distally extended position to a proximally retracted position relative to the syringe cylinder in order to render the syringe safe for disposal.

Having thus set forth the preferred embodiment, what is claimed is:

1. A syringe including a hollow cylinder having an open proximal end and a substantially closed distal end, a pre-filled ampule loaded into said cylinder through the proximal end thereof, said ampule having a sealed cap at one end thereof, and a double ended hypodermic needle loaded into said cylinder ahead of said ampule and arranged in spaced axial alignment with said ampule, said syringe also including:
   means for advancing said ampule axially and distally through said cylinder so that a proximal end of said needle penetrates the end cap of said ampule and a distal end of said needle projects outwardly from said cylinder past the distal end thereof; and
   locking means for releasably retaining said ampule at the distally advanced position within said cylinder, said locking means including at least one locking arm being pivotally connected to said syringe cylinder so as to be rotatable inwardly through an opening in said cylinder and towards said ampule to retain said ampule at said distally advanced position, said locking arm also being rotatable outwardly and away from said ampule for releasing said ampule from the distally advanced position.

2. The syringe recited in claim 1, wherein the means for advancing said ampule through said cylinder is a hollow collar surrounding at least some of said ampule and movable therewith through the proximal end of said cylinder, the distal movement of said collar through said cylinder causing a corresponding distal advancement of said ampule towards the proximal end of said needle.

3. The syringe recited in claim 2, wherein said locking means also includes a locking skirt extending outwardly from said collar, the locking arm of said syringe cylinder being rotatable into engagement with said locking skirt to releasably retain said ampule at said distally advanced position when said collar is moved distally through said cylinder.

4. The syringe recited in claim 1, wherein said cylinder includes an angled flange surrounding the open proximal end thereof, said flange being angled in a distal direction and located in spaced proximity to said locking arm, such that said locking arm is rotated inwardly of said cylinder and towards said ampule whenever a user's fingers are located in the space between said flange and said locking arm.

5. A syringe including a hollow cylinder having an open proximal end and a substantially closed distal end, a pre-filled ampule loaded into said cylinder through the proximal end thereof, said ampule having a sealed cap at one end thereof, and a double ended hypodermic needle loaded into said cylinder ahead of said ampule and arranged in spaced axial alignment with said ampule, said syringe also including:
   a needle cartridge in which said double ended needle is carried, said needle cartridge having a hollow sleeve surrounding said needle and oppositely disposed proximal and distal ends for supporting said needle in axial alignment with said ampule;
   means for advancing said ampule axially and distally through said cylinder so that a proximal end of said needle penetrates the end cap of said ampule and a distal end of said needle projects outwardly from said cylinder past the distal end thereof;
   first locking means for releasably retaining said ampule at the distally advanced position within said cylinder; and
   said second locking means for retaining the end cap of said ampule interconnected with the proximal end of said needle to prevent the detachment thereof after said needle penetrates said end cap.

6. The syringe recited in claim 5, wherein said second locking means for retaining the end cap of said ampule interconnected with the proximal end of said needle is a receptacle located at the proximal end of said needle cartridge sleeve, said receptacle being sized to receive the end cap of said ampule therewithin when said ampule is advanced distally through said cylinder.

7. The syringe recited in claim 6, wherein said receptacle has a lip formed therearound by which to engage the end cap of said ampule when said end cap is received within said receptacle.

8. The syringe recited in claim 5, further including normally relaxed compression spring means extending between the proximal and distal ends of said needle cartridge sleeve, the distal advancement of said ampule through said cylinder driving the proximal end of said sleeve toward the distal end thereof to compress said spring means therebetween and force the distal end of said needle outwardly from said sleeve and past the distal end of said cylinder so that an injection may be administered;
said spring means returning to the relaxed condition for driving the proximal end of said sleeve away from the distal end thereof to retract said needle within said sleeve when said first locking means releases said ampule from said distally advanced position.

9. The syringe recited in claim 5, further including third locking means for releasably retaining said needle cartridge at a relatively proximal position within said cylinder, so that the proximal end of said needle is supported for penetrating the end cap of said ampule when said ampule is advanced distally through said cylinder towards said cartridge.

10. The syringe recited in claim 9, wherein said third locking means comprises at least one leg pivotally connected to said cylinder and rotatable inwardly through an opening in said cylinder for engaging the sleeve of said needle cartridge at said relatively proximal position within said cylinder to prevent the distal advancement of said cartridge therethrough, said leg also being rotatable outwardly through said opening and out of engagement with said sleeve to release said needle cartridge and permit the distal advancement thereof through said cylinder.

11. The syringe recited in claim 9, further including fourth locking means for releasably retaining said needle cartridge at a relatively distal position within said cylinder, said fourth locking means comprising a locking tab pivotally connected to said cylinder and rotatable inwardly through an opening in said cylinder for engaging the sleeve of said needle cartridge at said relatively distal position to prevent the proximal displacement of said cartridge.

12. A syringe comprising a cylinder having an open proximal end and a substantially closed distal end and a fluid filled ampule loaded into said cylinder through the proximal end thereof, said syringe further comprising:
a needle cartridge loaded into said cylinder ahead of said ampule, said cartridge supporting a double ended hypodermic needle in spaced axial alignment with said ampule;
a hollow collar surrounding at least some of said ampule and capable of being moved distally through said syringe cylinder for correspondingly advancing said ampule distally through said cylinder and towards said needle cartridge such that a proximal end of said needle penetrates said ampule and a distal end of said needle extends outwardly from said cartridge and past the distal end of said cylinder so that the contents of said ampule can be expulsed therefrom; and
locking means movable to a locked position by which to releasably retain said ampule at the distally advanced position with said cylinder or movable to an unlocked position by which to release said ampule from the distally advanced position, so that said ampule can be disposed proximally through said cylinder and said needle retracted back into said cartridge.

13. The syringe recited in claim 12, wherein said locking means comprise a locking skirt extending outwardly from said collar; and
means connected to said cylinder for releasably engaging the locking skirt of said collar when said collar and ampule are moved together through said cylinder to said distally advanced position therewithin.

14. The syringe recited in claim 13, wherein the means connected to said cylinder for engaging the locking skirt of said collar includes at least one locking arm pivotally connected at one end thereof to said cylinder and having a catch formed at the other end;
said locking arm being pivotable inwardly through an opening in said cylinder for rotating said catch into engagement with said locking skirt to retain said ampule at the distally advanced position within said cylinder; and
said locking arm also being pivotable outwardly through said opening for rotating said catch out of engagement with said locking skirt to release said ampule from the distally advanced position.

15. The syringe recited in claim 14, wherein said cylinder includes an angled flange surrounding the open proximal end thereof, said flange being spaced from said locking arm, such that said locking arm is pivoted inwardly of said cylinder whenever a user's fingers are positioned in the space between said flange and said locking arm.

16. The syringe recited in claim 12, further comprising a receptacle located at a proximal end of said needle cartridge for receiving an end of said ampule therewithin when said ampule is moved distally through said cylinder and into engagement with said cartridge.

17. A syringe comprising a cylinder having an open proximal end and a substantially closed distal end and a fluid filled ampule loaded into said cylinder through the proximal end thereof, said syringe further comprising:
a needle cartridge loaded into said cylinder ahead of said ampule, said cartridge including a double ended hypodermic needle supported in spaced axial alignment with said ampule, said needle cartridge also including a sleeve surrounding said needle and having oppositely disposed proximal and distal ends for supporting said needle and compression spring means extending between said proximal and distal ends;
means for advancing said ampule distally through said cylinder and into engagement with said needle cartridge such that a proximal end of said needle penetrates said ampule and a distal end of said needle extends outwardly from said cartridge and past the distal end of said cylinder so that the contents of said ampule can be expulsed therefrom, the distal advancement of said ampule through said cylinder and into engagement with said cartridge also driving the proximal end of said sleeve toward the distal end thereof to compress said spring means therebetween and force the distal end of said needle outwardly from said sleeve and past the distal end of said cylinder so that an injection may be administered;

locking means movable to a locked position by which to releasably retain said ampule at the distally advanced position with said cylinder or movable to an unlocked position by which to release said ampule from the distally advanced position, so that said ampule can be disposed proximally through said cylinder and said needle retracted back into said cartridge; and said spring means returning to the relaxed condition for driving the proximal end of said sleeve away from the distal end thereof to retract said needle within said cartridge sleeve when said locking means releases said ampule from said distally advanced position.

18. A syringe including a hollow cylinder having an open proximal end and a substantially closed distal end, a pre-filled ampule loaded through the proximal end of said cylinder and movable therethrough, a needle cartridge loaded into said cylinder ahead of said ampule and movable through said cylinder, said cartridge supporting a double ended hypodermic needle in spaced axial alignment with said ampule, said syringe further including:

first locking means by which to releasably engage and retain said needle cartridge at a relatively proximal position within said cylinder;

means for moving said ampule into contact with said needle cartridge and into fluid communication with a proximal end of said needle thereof while said cartridge is retained at said relatively proximal position;

second locking means for preventing the detachment of said ampule from the needle of said needle cartridge;

third locking means by which to engage and retain said needle cartridge at a relatively distal position within said cylinder after said first locking means has released said cartridge from the relatively proximal position and said cartridge and ampule have been advanced distally through said cylinder; and fourth locking means by which to releasably engage and retain said ampule at said distally advanced position within said cylinder, such that a distal end of said needle is forced outwardly from said cartridge and past the distal end of said cylinder, the distal end of said needle being retracted back into said cartridge when said fourth locking means releases said ampule from said distally advanced position.

19. A syringe comprising a cylinder having an open proximal end and a substantially closed distal end and a fluid filled ampule loaded into said cylinder through the proximal end thereof, said syringe further comprising:

a needle cartridge loaded into said cylinder ahead of said ampule, said needle carrying cartridge including an outer sleeve surrounding a double ended needle and having means to retain said needle in spaced axial alignment with said ampule;

means for advancing said ampule axially and distally through said cylinder in a direction towards said cartridge until a first end of said needle penetrates said ampule and the opposite end of said needle is moved outwardly from the sleeve of said cartridge to project past the distal end of said cylinder for administering an injection; and locking means movable to either a locked position by which to releasably retain said ampule at the distally advanced position with said needle projecting from said cylinder or to an unlocked position by which to release said ampule from said distal position so that said needle can be retracted back into the sleeve of said cartridge.

20. The syringe recited in claim 19, wherein said locking means includes at least one locking arm being pivotally connected to said syringe cylinder so as to be selectively rotated inwardly of said cylinder in a direction towards said ampule for communicating with and retaining said ampule at the distally advanced position within said cylinder.

21. The syringe recited in claim 20, wherein said locking arm is a flexible member having a spring-like memory such that said locking arm is normally biased to rotate in a direction away from and out of communication with said ampule for releasing said ampule from said distally advanced position.

22. The syringe recited in claim 20, wherein said locking means further includes a collar surrounding said ampule and having a locking catch extending outwardly therefrom, said locking catch being engaged by said locking arm to retain said ampule at said distally advanced location within said cylinder after said locking arm has been rotated inwardly of said cylinder and towards said ampule.

23. The syringe recited in claim 19, wherein the means within the sleeve of said needle carrying cartridge for retaining said needle in axial alignment with said ampule are a pair of walls located at opposite ends of said sleeve, said needle extending between and being supported by said opposing walls.

24. The syringe recited in claim 23, wherein said needle carrying cartridge also includes compressible spring means located within said outer sleeve and extending between said pair of opposing walls.

25. The syringe recited in claim 24, wherein one of said pair of opposing walls is movable through the outer sleeve of said needle carrying cartridge relative to the other of said walls against the bias of said spring means so as to cause said spring means to be compressed between said walls, said ampule being advanced axially and distally through said cylinder so as to cause said movable wall to move through said sleeve.

26. The syringe recited in claim 25, wherein said needle carrying cartridge also includes a receptacle cooperating with and projecting in a proximal direction from said movable wall, whereby said ampule is received within and retained by said receptacle for preventing the removal of said needle from said ampule after said ampule has been moved distally through said syringe cylinder and into contact with the movable wall of said sleeve.

* * * * *